United States Patent [19]

Tait et al.

[11] 4,395,318

[45] Jul. 26, 1983

[54] PITTING CORROSION METER

[75] Inventors: William S. Tait, Racine, Wis.; Richard L. Martin; Richard A. Rodgers, both of St. Louis, Mo.

[73] Assignee: Petrolite Corporation, St. Louis, Mo.

[21] Appl. No.: 339,527

[22] Filed: Jan. 15, 1982

[51] Int. Cl.³ ..................... G01N 27/30; G01N 27/46
[52] U.S. Cl. .................................. 204/404; 204/1 T; 204/406; 204/412
[58] Field of Search ........................... 204/1 C, 195 C

[56] References Cited

U.S. PATENT DOCUMENTS

| 3,660,249 | 5/1972 | Townsend | 204/1 T |
| 3,855,101 | 12/1974 | Wilson | 204/195 R |
| 3,878,064 | 4/1975 | Weisstuch et al. | 204/1 T |
| 4,056,445 | 11/1977 | Gauntt et al. | 204/1 T |
| 4,294,667 | 10/1981 | Yamamoto et al. | 204/1 T |

OTHER PUBLICATIONS

W. S. Tait, "Comparison of Potentiodynamically Determined Pitting Rates with Actual Pitting Rates for Mild Steel & Admiralty Brass in Oxygen Bearing Water", Corrosion, vol. 34 (6), pp. 214-218 (1978).
R. L. Martin "Potentiodynamic Polarization Studies in the Field", Materials Performance, vol. 18 (3), pp. 41-50 (1979).
L. G. Gainer et al., "An Apparatus for the Examination of Localized Corrosion Behavior", Corrosion, vol. 35 (2), pp. 61-67 (1979).

Primary Examiner—Aaron Weisstuch
Attorney, Agent, or Firm—Sidney B. Ring; Hyman F. Glass; Leon Zitver

[57] ABSTRACT

Test, auxiliary and reference electrodes are immersed in a corrodant fluid. The test electrode is cathodically polarized by a cathodic polarization circuit. Peak current flow in the auxiliary electrode is measured and a linear cathodic polarization function is generated by a computer circuit. The test electrode is forwardly and reversely anodically polarized by an anodic polarization circuit. A comparator circuit senses the voltage of the test electrode with respect to the auxiliary electrode during reverse anodic polarization and compares this value to the cathodic polarization function. When the test electrode voltage and cathodic polarization function are equal, an anodic memory circuit stores the value of the current passing through the test electrode. This current is the pitting current which is converted into pitting rate.

29 Claims, 9 Drawing Figures

PITTING CORROSION METER

BACKGROUND OF THE INVENTION

This invention relates to measuring and testing of pitting corrosion and it relates particularly to the instruments and electrochemical techniques used in monitoring pitting corrosion.

Two types of metallic corrosion are prevalent in aqueous systems. They are known as general and pitting corrosion. General corrosion proceeds uniformly over the metal surface at a relatively low rate. General corrosion rates are readily measurable with such methods as described in U.S. Pat. No. 3,687,610 to Gilson et al (Weight Loss) and U.S. Pat. No. 3,406,101 to Kilpatrick (Linear Polarization). Instrumentation used for linear polarization is like that described in U.S. Pat. No. 3,661,751 to Wilson.

Pitting corrosion proceeds 10–1000 times faster than general corrosion and occurs at small discrete areas rather than continuously over the metal surface. Because pitting occurs discontinuously on the metal surface, neither weight loss nor linear polarization can be utilized to measure its rate. Special methods of measurement need be employed.

Two such methods are physical measurement and non-linear polarization. Physical measurement involves determining the pit depth in mils (1,000 mils = 1 inch) and dividing this depth by the total time (in years) during which the metal was exposed to the corrosive fluid. This gives the pitting rate in mils penetration (of the metal) per year. This method has the inherent disadvantage of being an "after-the-fact" type of determination. Measurement cannot be made in advance of the corrosion in order that corrective action can be taken. Also the process under surveillance for pitting corrosion must be stopped in order to make this measurement.

A more desirable method of pitting rate determination is non-linear polarization. With this method, pitting rates can be measured "as-they-happen" rather than "after-the-fact". Thus, corrective action can be taken to avoid premature equipment failure by a pit which has finally penetrated the metal. Non-linear polarization has the disadvantage of being time consuming. The person utilizing the method must also have some expertise of corrosion phenomena as it relates to non-linear polarization. In addition, specialized equipment is required.

In order to adequately describe our invention we need to discuss the non-linear polarization method in more detail.

Three or four pieces of an appropriate metal, hereafter referred to as electrodes, are attached to a holder in the manner described in the above mentioned U.S. Pat. No. 3,406,101 to Kilpatrick, U.S. Pat. No. 3,558,462 to Wilson, U.S. Patent No. 3,639,876 to Wilson and U.S. Pat. No. 3,632,495 to Watson et al. The electrodes (when four are used) are designated as reference, anodic test, cathodic test and auxiliary electrodes. At least the test electrodes are made of the metal whose properties in respect to pitting corrosion are to be monitored. The electrodes are inserted into the corrosive fluid for the pitting measurement and the test electrodes brought into equilibrium with the fluid.

The method is as follows:

The cathodic test electrode is increasingly polarized cathodically with respect to the probe body or the reference electrode until the applied potential is approximately −300 millivolts from the rest potential. As the potential is increased, the current which is required to be passed between the auxiliary electrode and the test electrode in order to maintain the potential between the latter and the probe body or reference electrode is recorded as a function of the applied potential in the form of a semi-log plot of current versus potential. This is referred to as the cathodic curve. After the cathodic curve is generated, the anodic test electrode is increasingly polarized anodically in a similar manner to the polarization of the cathodic test electrode. When the current passed between the test electrode and the auxiliary electrode is 50 milliamps, the potential is driven back towards the rest potential until 0 milliamps current is passed between these electrodes. As with the cathodic polarization, the anodic polarizations are plotted against current. This gives forward and reverse anodic curves. The intersection of the reverse anodic curve with the cathodic curve or its extrapolation yields the pitting current. The pitting current is converted into pitting rate (mils penetration per year), e.g., by using the following equation for standard size (9 cm$^2$) electrodes: mils penetration per year = (1000) × (Pitting Current).

Further discussion of this technique and a comparison of pitting rates obtained in this manner with actual rates can be found in the following publications:

R. L. Martin, CORROSION/77, (International Corrosion Forum, Mar. 14–18, 1977, San Francisco, California), Paper No. 140

W. S. Tait, CORROSION, Vol. 34, No. 6, pp. 214–218 (1978)

R. L. Martin, MATERIALS PERFORMANCE, Vol. 18, No. 3, pp. 41–50 (1979)

The non-linear polarization can be performed in discrete steps or continuously.

It is an object of this invention to provide an instrument capable of determining pitting rates automatically and repetitively without the need to plot the anodic and cathodic curves. It is a further object of this invention to provide such an instrument which requires no corrosion expertise in order to obtain pitting rates with it. Other objects of the invention will become apparent from the following description.

SUMMARY OF THE INVENTION

In accordance with the invention there is provided a pitting corrosion meter comprising, in one embodiment, electrode means, e.g., one or two test electrodes, a reference electrode and an auxiliary electrode, the electrode means being adapted for immersion in a corrodant fluid; cathodic circuit means for cathodically polarizing a test electrode to a predetermined negative voltage with respect to the reference electrode and holding it at that potential for a predetermined period of time thereby causing current flow in the auxiliary electrode; first monitoring means for monitoring and storing the peak value of the resulting current between the test and auxiliary electrodes, such peak value corresponding to a point on a cathodic curve (semi-log plot of current versus potential); a computer circuit for generating the cathodic curve and its extrapolation from one such reading and from stored information as to the slope of said curve, or from two such readings at different predetermined negative voltages; an anodic circuit for increasing the current or potential between a test and auxiliary electrodes, preferably at a fixed rate, to a predetermined value in order to anodically polarize the test electrode with respect to the reference electrode and then decreasing the current or potential at a fixed rate; a second monitoring circuit for monitoring the potential of the test electrode with respect to the reference electrode at the respective values of the current during the decreasing polarization of the test electrode, thereby generating a reverse anodic curve; and a comparator circuit for determining the intersection of the reverse anodic curve with the cathodic current curve extrapolation, the value of the current at such intersection being that of the pitting current which is proportional to pitting rate. In a preferred embodiment, circuitry for displaying and/or recording the pitting rate, and timing means, e.g., timing circuitry in the form of a repeat/-delay circuit, cathodic timing circuit and recorder timing circuit, for directing operation of the invention, are provided.

The displaying and recording circuitry is preferably adapted to record and/or display the pitting rate for a predetermined period of time and the repeat/delay circuit is adapted to place the meter on standby for a predetermined time period and to again initiate the measurement process at the expiration of that time period.

Where two test electrodes are employed, one is used for the cathodic polarization and the other for the anodic polarization.

For accuracy, the meter should be employed with the test electrode essentially in equilibrium with the corrodant at the start of both the cathodic and anodic polarizations.

The invention also encompasses the individual circuit means for carrying out the various functions of the apparatus.

DESCRIPTION OF THE SPECIFIC EMBODIMENTS

The invention is illustrated by, but not limited to the exemplary embodiments described below. Referring to the drawings.

DESCRIPTION OF THE PREFERRED EMBODIMENT

Figure 1:
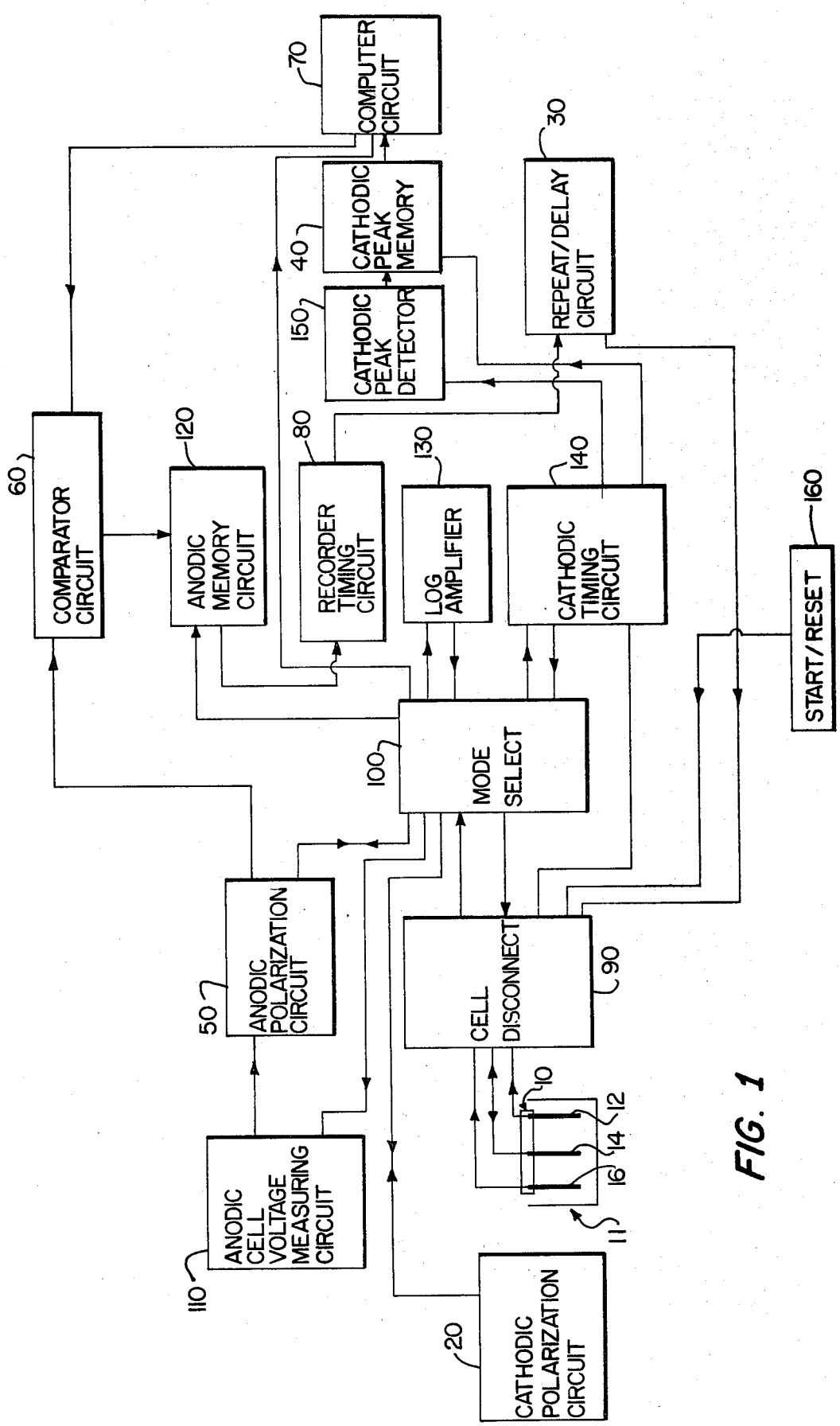
FIG. 1 is a block diagram setting forth the operational sequence of the invention.

Now with reference to the drawings, a pitting corrosion meter built according to the principles and concepts of the present invention will be described in detail. With attention being directed in particular to FIG. 1, it will be seen that the pitting corrosion meter includes a cell 11 having a probe 10 provided with a plurality of electrodes. Specifically, probe 10 comprises reference electrode 12, test electrode 14, and auxiliary electrode 16. Electrodes 12, 14 and 16 are directly connected to cell disconnect circuit 90. Cell disconnect ciruit 90 is operative to place probe 10 into and out of electrical communication with the mode select circuit 100. Mode select circuit 100 receives signals from the cathodic polarization circuit 20 and anodic polarization circuit 50, and selectively applies these signals to probe 10. Mode select circuit 100 also receives signals from probe 10 and selectively passes these signals to the anodic cell voltage measuring circuit 110, log amplifier 130, cathodic polarization circuit 20, and anodic polarization circuit 50.

The cathodic timing circuit 140 generates timing signals which are applied to mode select circuit 100, a cathodic peak detector circuit 150 and a cathodic peak memory circuit 40. Additional timing signals are produced by the repeat/delay circuit 30 and applied to cell disconnect circuit 90 in response to signals received from a recorder timing circuit 80 and mode select circuit 100.

Recorder timing circuit 80 transmits a calculated pitting current signal to a recorder (not shown). The calculated pitting current signal is generated by a comparator circuit 60 which receives inputs from anodic polarization circuit 50 and a computer circuit 70. Computer circuit 70 is an analog module which produces an analog function based on a value sensed by the cathodic peak detector 150 and stored in cathodic peak memory 40.

Operation of the meter of the present invention is initiated by actuation of a start/reset circuit 160. Cell disconnect circuit 90 is thereby energized connecting probe 10 to cathodic polarization circuit 20 through mode select circuit 100. Cathodic timing circuit 140 and log amplifier 130 are also activated through mode select circuit 100 at this time. Cathodic polarization circuit 20 impresses a negative voltage on test electrode 14 with respect to reference electrode 12. This voltage may suitably be approximately −0.100 v below the rest potential and is held for a period of approximately 120 seconds. The period of excitation of test electrode 14 is controlled by cathodic timing circuit 140. A signal indicative of the value of the probe current passing through auxiliary electrode 16 due to the voltage applied to test electrode 14 is passed by mode select circuit 100 to log amplifier 130, which converts the current signal to a signal indicative of the log of the probe current. Mode select circuit 100 passes the log of the probe current to cathodic timing circuit 140 which operates to pass this signal to cathodic peak detector circuit 150 during the last 30 seconds of the 120 second period of excitation of test electrode 14. Circuit 150 measures the maximum probe current occurring during this 30 second period and passes this value to cathodic peak memory circuit 40 which stores the peak measured value. This stored peak value of the log of the probe current is shown as point A in FIG. 8. At the end of the 120 second period of cathodic polarization, cathodic timing circuit 140 automatically and simultaneously switches itself off and switches the state of mode select circuit 100 to connect anodic polarization circuit 50 through cell disconnect circuit 90 to probe 10.

Figure 8:
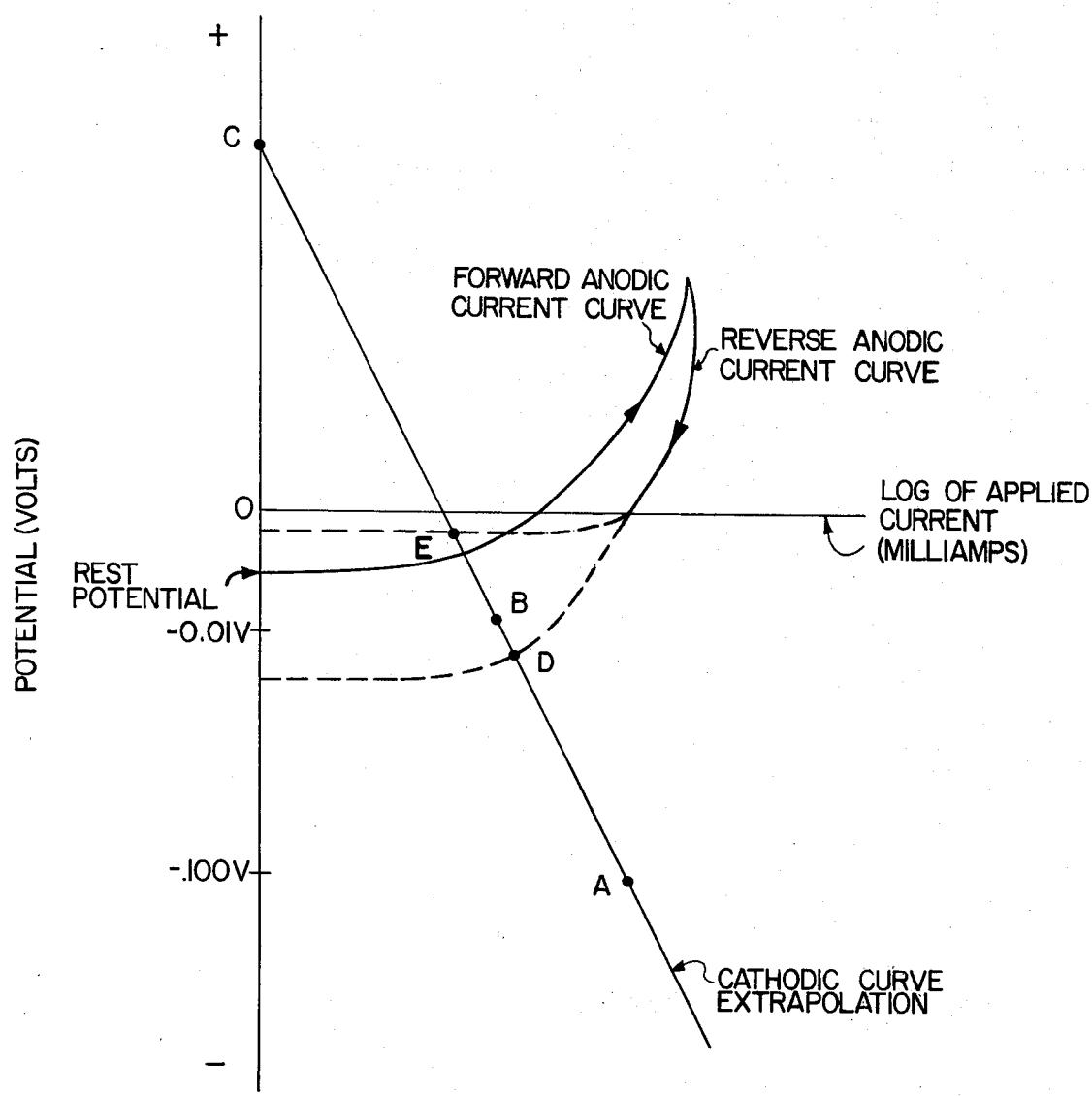
FIG. 8 is a graph showing voltage of the test electrode in volts as the ordinate axis versus log of current in milliamperes between the test and auxiliary electrodes as the abscissa for the purpose of explaining the operation of the meter of the present invention.
Figure 2:
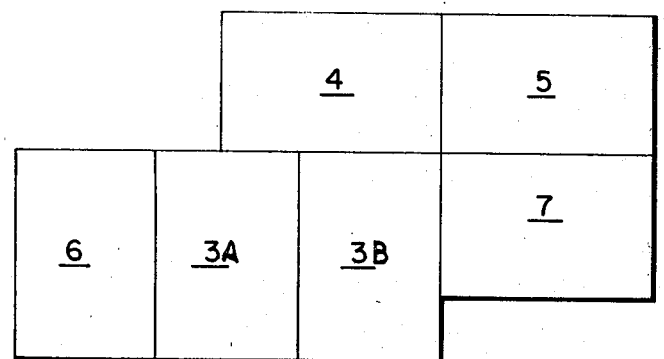
FIG. 2 is a diagrammatic representation showing the proper orientation of FIGS. 3A through 6 for forming a detailed schematic diagram of the invention.

Anodic polarization circuit 50 increases the current through test electrode 14 at a linear rate from rest potential to approximately 50 ma as shown graphically in FIG. 8 by the forward anodic current curve. The rate of current increase is controlled by circuit 50, which is adjustable from 2 ma per minute to 10 ma per minute. When the current level reaches 50 ma, the current is progressively decreased at the same rate as the rate of increase. The decreasing current is shown graphically in FIG. 2 as the reverse anodic current curve.

The reverse anodic polarization current is logarithmically converted in log amplifier 130 and passed to computer circuit 70. Computer circuit 70 also receives the peak cathodic current from memory circuit 40. As the anodic current decreases, computer circuit 70 continuously calculates the voltage which corresponds to a straight line passing through point A (FIG. 8) and corresponds to the instantaneous value of the anodic current. The function generated is shown in FIG. 8 as the cathodic curve extrapolation. The cathodic curve extrapolation has a slope equal to an empirically derived value and can range from 0.060 v per decade of current to 10 v per decade.

Anodic cell voltage measuring circuit 110 is connected through mode select circuit 100 and cell disconnect circuit 90 to probe 10 during anodic polarization. Circuit 110 produces a signal indicative of the voltage of test electrode 14 as compared to reference electrode 12. This signal is transmitted through polarization circuit 50 during the reverse anodic polarization to comparator circuit 60.

Comparator circuit 60 also receives the output from computer circuit 70. Comparator circuit 60 generates an output when the signals from circuits 70 and 110 intersect as shown in FIG. 8 at a point such as D or E, as explained below. An output from comparator 60 also resets all previously described circuits to their initial states.

The output from comparator circuit 60 activates anodic memory circuit 120. Circuit 120 receives and stores a signal indicative of the log of the current generated by circuit 50 at the time an output is generated by comparator circuit 60. This stored signal is the pitting current signal and is made available to a recorder (not shown). The scale factor of the recorder is adjusted so that the recorded signal is the pitting rate.

Recorder timing circuit 80 is activated by an output from comparator circuit 60 through anodic memory circuit 120. Recorder timing circuit 80 simultaneously starts the recorder motor (not shown), applies the pitting current signal to the recorder, and starts the recorder timing sequence. At the end of one minute, the recorder is shut off, the pitting current signal is removed, the anodic memory circuit 120 is deactivated, and a pulse signal is sent to repeat/delay circuit 30.

Repeat/delay circuit 30 can be in one of two modes of operation. In the stop mode, the pulse received from circuit 80 has no effect and the meter operation ceases. In the repeat mode a signal is sent, after a predetermined delay time, to cell disconnect circuit 90. This signal reactivates the meter and the sequence described above is repeated.

Figure 3A:
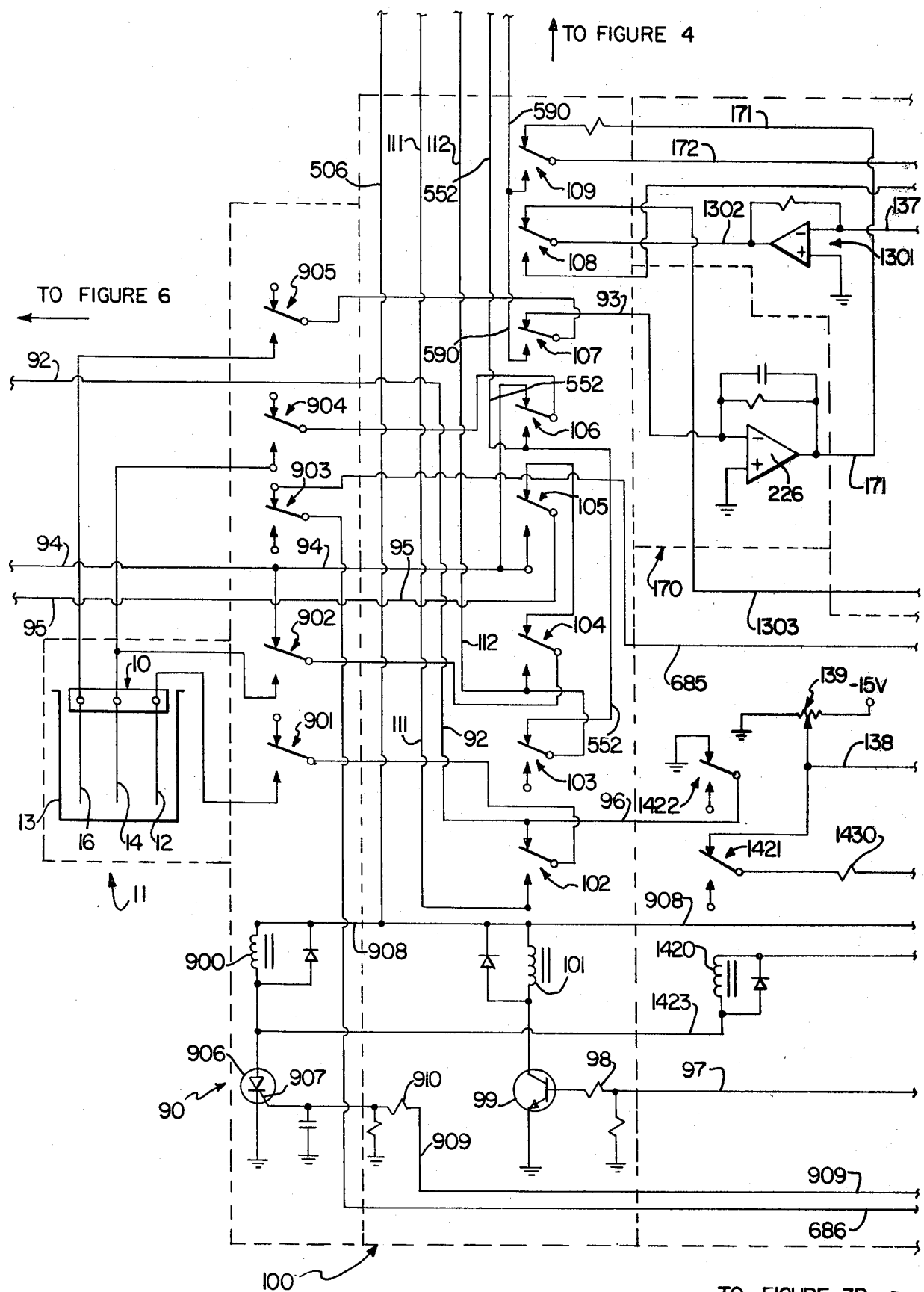
FIGS. 3A and 3B are detailed schematic diagrams of a cell, cell disconnect circuit, mode select circuit, cathodic timing circuit, and log amplifier of the present invention.
Figure 3B:
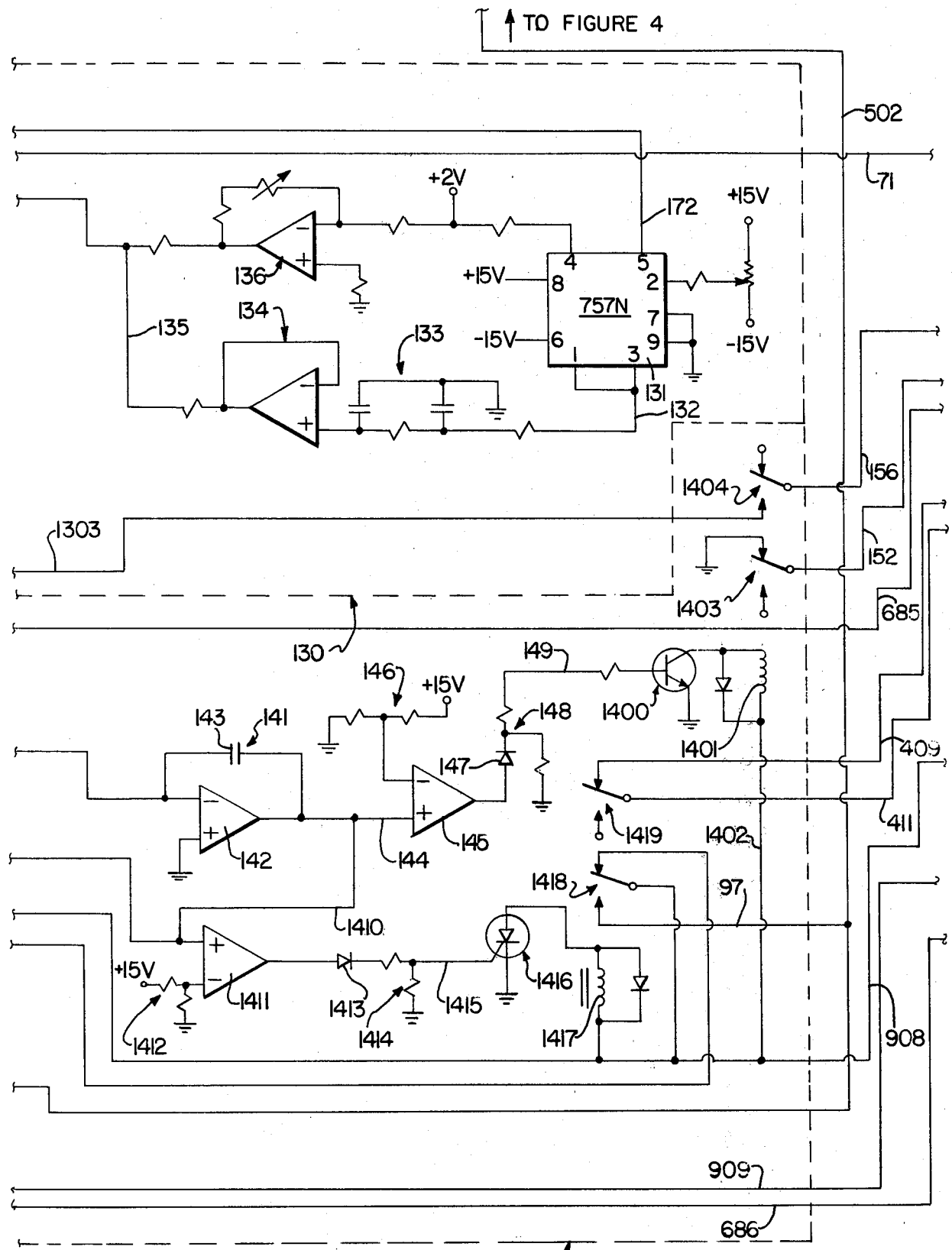
Figure 7:
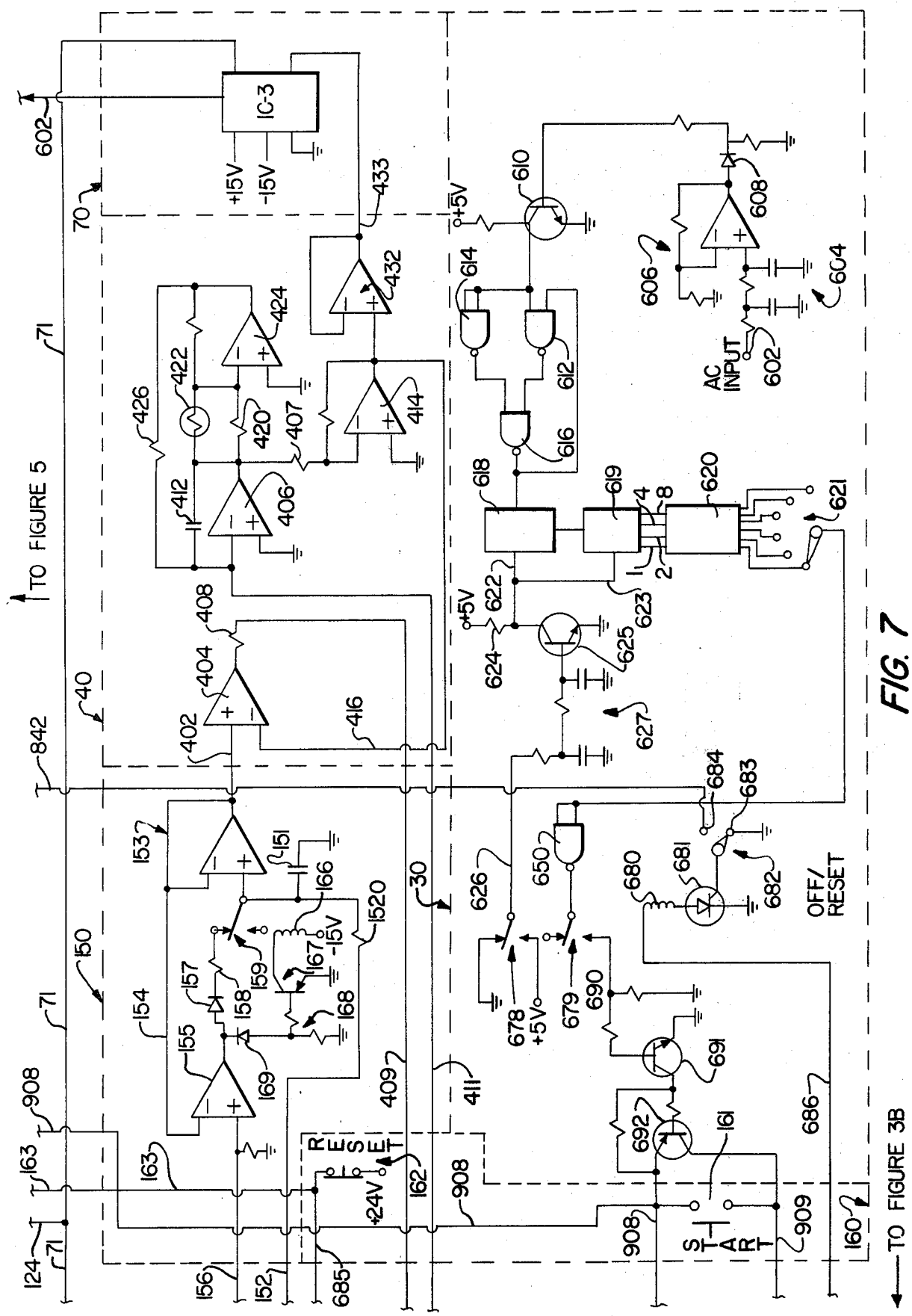
FIG. 7 is a detailed schematic diagram of the start/reset circuit, cathodic peak detector circuit, cathodic peak memory circuit, computer circuit and repeat/delay circuit of the present invention.

Referring now to FIGS. 3A, 3B and 7, it will be seen that cell 11 comprises a probe 10 disposed in tank 13. Probe 10 includes reference electrode 12, test electrode 14 and auxiliary electrode 16. The electrodes are immersed in corrosive fluid disposed in tank 13. Each of the electrodes is separately connected to cell disconnect circuit 90.

Cell disconnect circuit 90 comprises a relay having contactors 901-905 operated by relay coil 900. Relay coil 900 is energized through thyristor 906 by the application of a positive voltage to gate 907 of the thyristor. The cathode of thyristor 906 is connected to ground and the anode is connected to one terminal of relay coil 900. The opposite terminal of relay coil 900 is connected to a 24 v supply on line 908. The 24 v supply on line 908 is derived from start/reset circuit 160. Gate 907 is connected to start/reset circuit 160 through line 909 and resistor 910. Start/reset circuit 160 is shown in FIG. 7 to comprise a normally open momentary contact start switch 161 disposed across lines 908 and 909.

In operation, start switch 161 is depressed to activate cell disconnect circuit 90 by applying 24 v through resistor 910 to gate 907. Coil 900 is thus energized moving contactors 901-905 to their normally open positions. Electrodes 12, 14, and 16, which are connected to the normally open terminals of contactors 901, 902 and 904, and 905, are thereby connected to mode select circuit 100.

Start/reset circuit 160 also contains a normally closed momentary actuation reset switch 162. One terminal of switch 162 is connected to a 24 v supply. The other terminal of switch 162 is connected through line 163 and recorder timing circuit 80 (shown in FIG. 5), to be discussed hereinafter, to line 908. Accordingly, when switch 162 is depressed, voltage is removed from line 908 and relay coil 900 is deenergized. This also causes thyristor 906 to be reset.

Mode select circuit 100 comprises a relay having a coil 101 and contactors 102-109. As shown, mode select circuit 100 is in the first operational state wherein all contactors 102-109 are in their normally closed positions. One terminal of relay coil 101 is connected to a 24 v supply through line 908. The other terminal of relay coil 101 is connected to the collector of transistor 99. The emitter of transistor 99 is connected to ground and the base of transistor 99 is connected through resistor 98 and the line 97 to cathodic timing circuit 140. Accordingly, mode select circuit 100 is moved to its second operative state wherein contactors 102-109 are in their normally open positions by energization of relay coil 101 through transistor 99 being turned on. Transistor 99 is turned on by cathodic timing circuit 140 as will be discussed hereinafter.

Figure 6:
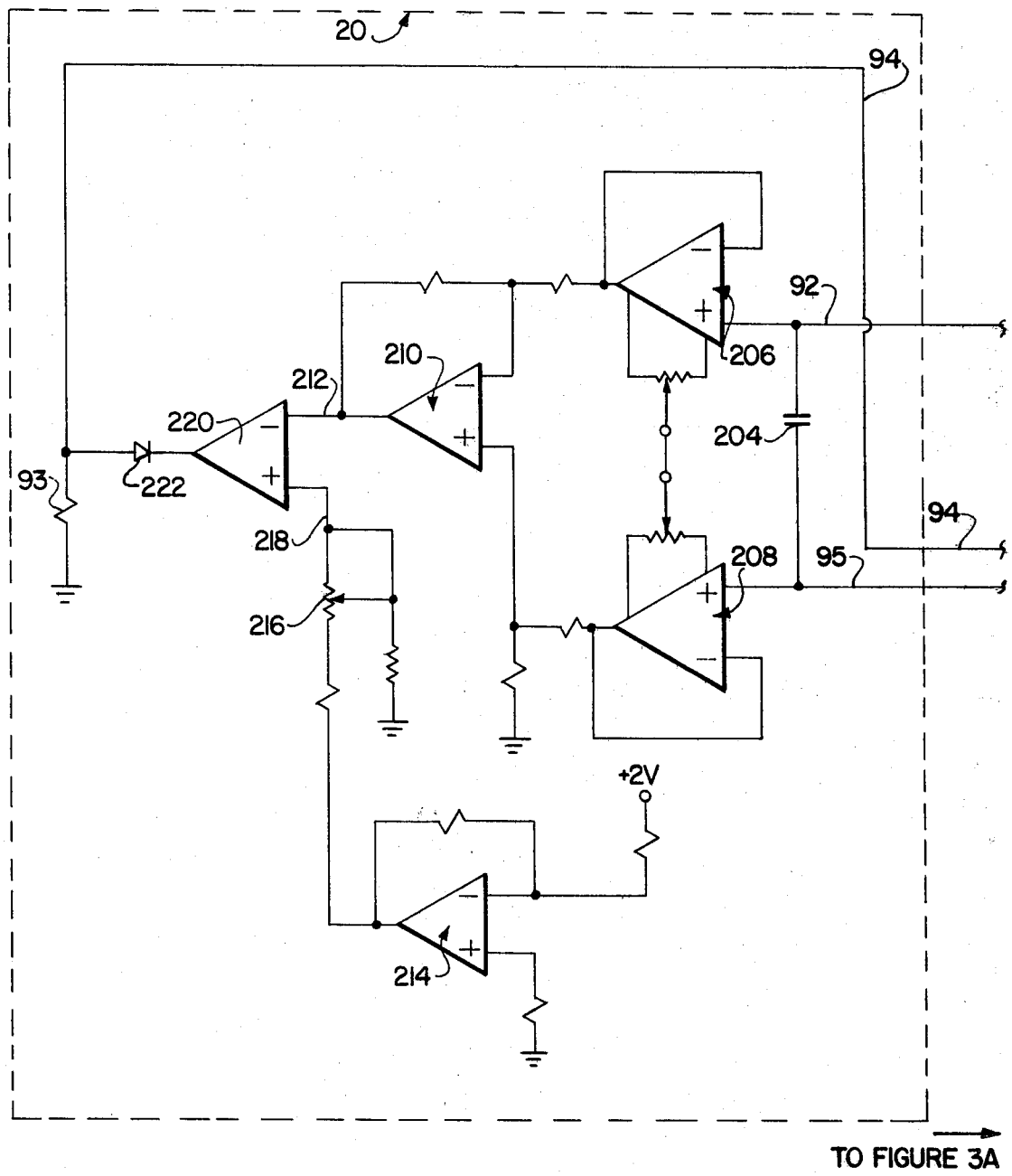
FIG. 6 is a detailed schematic diagram of the cathodic polarization circuit of the present invention.

In operation, when cell disconnect circuit 90 is activated and mode select circuit 100 is in the first operative state, reference electrode 12 is connected through contactors 901, 102 and line 96 to cathodic timing circuit 140 and through contactors 901, 102 and line 92 to polarization circuit 20 (see FIG. 6). Test electrode 14 is connected through contactor 902, contactor 104, contactor 105 and line 95 to cathodic polarization circuit 20. Test electrode 14 is also connected through contactor 904, contactor 106 and line 94 to cathodic polarization circuit 20. Auxiliary electrode 16 is connected through contactor 905, contactor 107 and line 93 to sensing amplifier 170.

Cathodic polarization circuit 20 is seen in FIG. 6 to comprise buffer amplifiers 206 and 208 connected to receive signals from the reference electrode 12 and test electrode 14, repectively, on lines 92 and 95. A capacitor 204 is connected between lines 92 and 95 to filter spurious signals. The outputs from amplifiers 206 and 208 are passed to the inverting and non-inverting inputs of a differential amplifier 210, respectively. Accordingly, the output at differential amplifier 210 is indicative of the voltage difference between the reference electrode 12 and the test electrode 14. This voltage difference signal is supplied through line 212 to the inverting input of amplifier 220. The signal on line 212 is compared with a reference potential on line 218. The reference potential is derived from a 2 v source and inverted in amplifier 214. The output of amplifier 214 is adjusted to the desired level of approximately −0.100 v by potentiometer 216. Amplifier 220 compares the signals on lines 212 and 218 and impresses a negative voltage on the test electrode 14 through diode 222 and line 94 in response to the voltage difference sensed. Accordingly, test electrode 14 is maintained at a potential of approximately −0.100 v with respect to reference electrode 12. The period of application of the −0.100 v is called the cathodic polarization phase.

The length of the cathodic polarization phase is determined by cathodic timing circuit 140 (FIGS. 3A and 3B). Cathodic timing circuit 140 includes a timing integrator 141 which comprises operational amplifier 142 and timing capacitor 143. An input signal is derived from variable resistor 139 which is connected between a −15 v source and ground. The input signal is delivered through line 138 to the inverting input of amplifier 142. The output of timing integrator 141 is passed through line 144 to the noninverting input of operational amplifier 145. Amplifier 145 compares this output to a signal derived from a 15 v supply and voltage divider network 146. The output from amplifier 145 is delivered via diode 147, resistor network 148, and line 149 to transistor 1400. The emitter of transistor 1400 is connected to ground while the collector of transistor 1400 is connected to one terminal of relay coil 1401. The opposite terminal of relay coil 1401 is connected through line 1402 and line 908 to a 24 v supply. Relay coil 1401 operates contactors 1403 and 1404 shown in their normally closed positions.

In a similar manner, the output of amplifier 142 is passed through line 1410 to the noninverting input of operational amplifier 1411. Amplifier 1411 compares this output to a signal derived from a 15 v source and voltage divider 1412. The output from amplifier 1411 is delivered through diode 1413, voltage divider 1414 and line 1415 to the gate of thyristor 1416. The cathode of thyristor 1416 is connected to ground and the anode is connected to one terminal of relay coil 1417. The opposite terminal of coil 1417 is connected through line 908 to a 24 v source. Coil 1417 operates contactors 1418 and 1419.

Cathodic timing circuit 140 also includes a relay comprising a relay coil 1420 and contactors 1421 and 1422. One terminal of coil 1420 is connected through line 1423 to the anode of thyristor 906. The other terminal of coil 1420 is connected to contactor 1418. Contactor 1421 is operative in the normally closed position, as shown, to insert a resistor 1430 in parallel with timing capacitor 143 to discharge that capacitor.

In operation, relay coil 1420 is energized when thyristor 906 is activated. Contactors 1421 and 1422 move to their normally open positions and capacitor 143 begins to charge. After approximately 90 seconds, the output of the timing integrator reaches the level set by voltage divider 146 and amplifier 145 outputs a signal through line 149 which turns transistor 1400 on to energize relay coil 1401. Relay coil 1401 causes contactors 1403 and 1404 to assume their normally open positions. The function of contactors 1403 and 1404 will be discussed hereinafter.

After approximately 120 seconds, the output on line 1410 reaches the level set by voltage divider 1412. This causes an output from amplifier 1411 to activate thyristor 1416. Thyristor 1416 energizes relay coil 1417 which causes contactors 1418 and 1419 to assume their normally open states. Contactor 1418 removes power from relay coil 1420 causing contactors 1421 and 1422 to assume their initial states thereby resetting circuit 140. Also, contactor 1418 supplies power to transistor 99 causing mode select circuit 100 to assume its second operational state. Thyristor 1416 remains activated until the power through line 908 is interrupted either by activation of reset switch 162 (FIG. 7) or by operation of the comparator circuit 60, as will be discussed hereinafter.

When contactor 1421 assumes its initial state, capacitor 143 is discharged through resistor 1430. When contactor 1422 assumes its initial state, and disconnect circuit 90 is deactivated (as explained below), capacitor 204 (FIG. 6) is discharged also. Contactor 1422 completes a discharge circuit for capacitor 204 through line 95, contactors 105, 104, and 902, line 94, resistor 93, and ground to lines 96 and 92.

During the cathodic polarization phase, current produced in auxiliary electrode 16 due to the polarization of test electrode 14 is passed through contactor 905 and contactor 107 to sensing amplifier 170 through line 93. Amplifier 170 inverts the current signal, amplifies it and passes it through line 171, contactor 109 and line 172 to logarithmic amplifier 130.

Log amplifier 130 includes a type 757 N integrated circuit 131 (sold by Analog Devices, Inc.) which receives the current signal on line 172. IC 131 outputs a signal on line 132 which passes through filter network 133 and buffer amplifier 134 to line 135. The signal on line 135 is added to an offset signal generated by a 2 v supply and an adjustable offset amplifier 136 resulting in a log I signal on line 137. The log I signal is inverted and amplified in amplifier 1301 and delivered through line 1302, contactor 108 and line 1303 to the normally open terminal of contactor 1404.

As discussed above, after 90 seconds of operation, cathodic timing circuit 100 energizes relay coil 1401 causing contactor 1404 to assume its normally open position thereby delivering the log I signal on line 1303 through line 156 to cathodic peak defector circuit 150 (FIG. 7).

As seen in FIG. 7, cathodic peak detector circuit 150 includes a storage capacitor 151. Capacitor 151 can be discharged through a resistor 1520, line 152 and contactor 1403 of timing circuit 140. Any charge on capacitor 151 is sensed at the noninverting input of a buffer amplifier 153. The output of amplifier 153 is fed through line 154 to the inverting input of operational amplifier 155. The noninverting input of operational amplifier 155 is connected through line 156 to contactor 1404 of timing circuit 140. The output of amplifier 155, when positive, is fed through a diode 157, resistor 158, and the normally closed terminal of relay contactor 159 to capacitor 151, which is charged thereby.

When the output of amplifier 155 is negative, it passes through diode 169 and resistor network 168 to transistor 167. Transistor 167 energizes relay coil 166 which moves contactor 159 to its normally open position.

In operation, as discussed above, timing circuit 140 (FIGS. 3A,3B) moves contactors 1403 and 1404 to their normally open positions after 90 seconds. Accordingly, capacitor 151 is ready to be charged and the log I signal is transmitted through line 156 to amplifier 155 at this time. When the charge on capacitor 151 is less than log I, the signal on line 154 is less than the signal on line 156. Thus, the output of amplifier 155 is positive and capacitor 151 is charged to a higher level equal to log I. When the charge on capacitor 151 is greater than log I, the signal on line 154 is greater than the signal on line 156 and the output of amplifier 155 is negative. Accordingly, relay coil 166 is energized and contactor 159 is moved to its normally open position and the charge on capacitor 151 remains constant. Consequently, it can be seen that the charge on capacitor 151 and thus the output of buffer amplifier 153 on line 402 are always equal to the maximum value of log I.

The maximum log I output of amplifier 153 is supplied through line 402 to cathodic peak memory circuit 40. Cathodic peak memory circuit 40 receives the signal on line 402 at the noninverting input of operational amplifier 404. The output of amplifier 404 is passed through resistor 408, line 409, the normally closed terminal of contactor 1419 (FIG. 3B) and line 411 to the inverting input of amplifier 406 which operates as an integrator with memory capacitor 412 connected from the output to inverting input. The output of amplifier 406 is passed through resistor 407, inverting amplifier 414 and line 416 to the inverting input of amplifier 404 where it is compared with the maximum log I input on line 402. The output of inverting amplifier 414 is also passed through buffer amplifier 432 through line 433 to computing circuit 70.

The signal stored on capacitor 412 is temperature stabilized by positive feedback from inverting amplifier 424. Amplifier 424 receives an input signal from amplifier 406 through a parallel combination of resistor 420 and thermistor 422. The output of amplifier 424 is passed through resistor 426 to the inverting input or amplifier 406.

In operation, memory capacitor 412 is charged to a voltage indicative of the maximum log I signal on line 402 by a signal received from amplifier 404. Amplifier 404 develops this charging signal by comparing a signal indicative of the charge on capacitor 412 received on line 416 with the maximum log I signal received on line 402. Any variation in the stored voltage on capacitor 412 caused by, for example, leakage current in capacitor 412, leakage current through amplifier 406 or variations in temperature are compensated for by positive feedback developed by amplifier 424. At the end of the 120 second timing period of cathodic timing circuit 140 (FIGS. 3A and 3B), contactor 1419 moves to the normally open position and the charging of capacitor 412 ceases. The charge on capacitor 412 is thus indicative of the maximum log I signal. This signal is stored and made available to computing circuit 70 through line 433 during the anodic polarization phase, to be discussed below.

Figure 4:
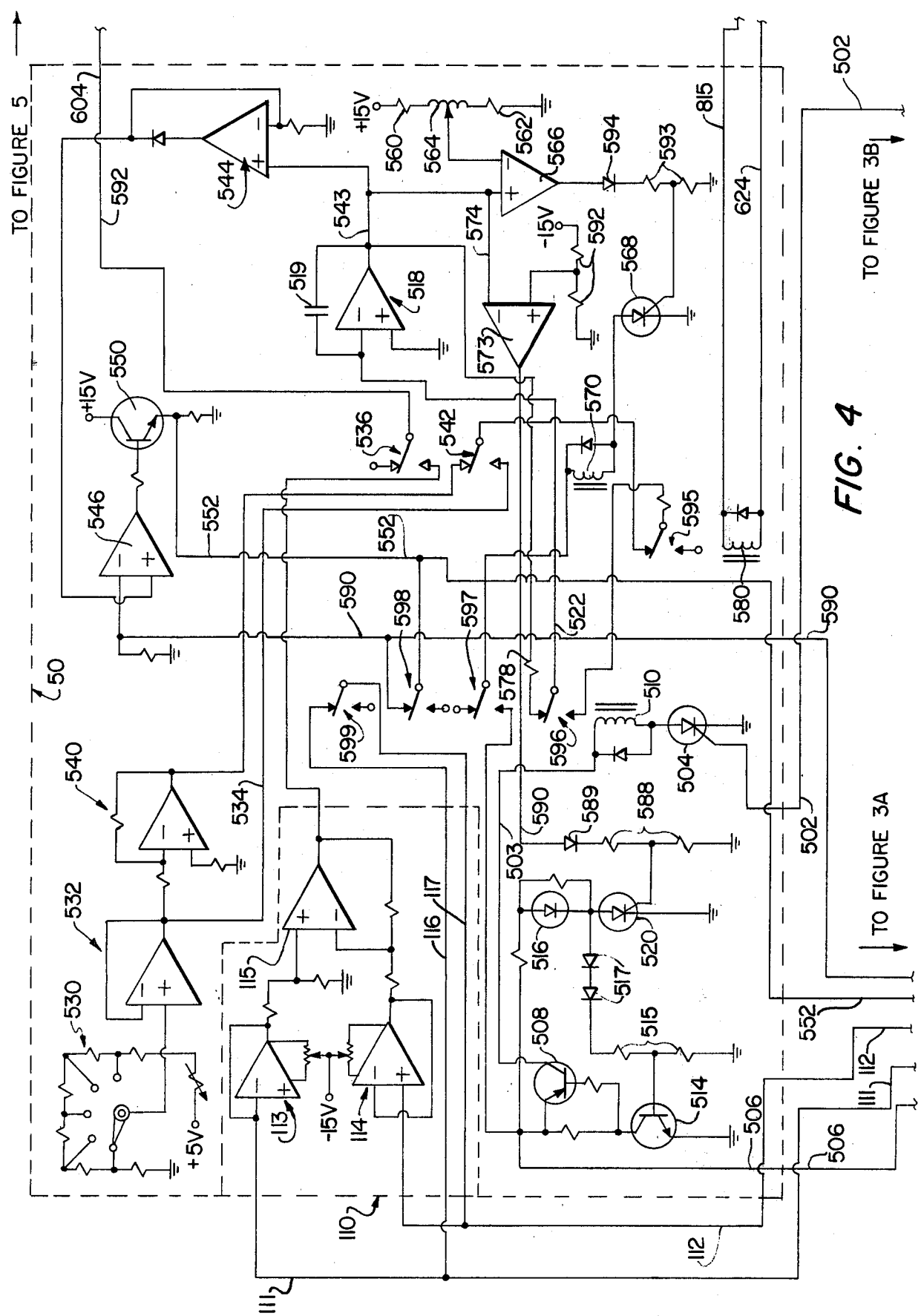
FIG. 4 is a detailed schematic diagram of the anodic cell voltage measuring circuit and the anodic polarizing circuit of the present invention.

The anodic polarization phase begins when mode select circuit 100 (FIG. 3A) is moved to its second operational state by cathodic timing circuit 140, as discussed above. In the second operational state, mode select circuit 100 connects reference electrode 12 through contactors 901 and 102, and line 111 to anodic cell voltage measuring circuit 110 (FIG. 4). Similarly, test electrode 14 is connected through contactors 902 and 104, and line 112 to anodic cell voltage measuring circuit 110. Test electrode 14 is also connected through contactor 904, contactor 106 and line 552 to anodic polarizing circuit 50 (FIG. 4). Auxiliary electrode 16 is connected through contactor 905, contactor 107 and line 590 to anodic polarizing circuit 50. Auxiliary electrode 16 is also connected through line 590 and contactor 109 to logarithmic amplifier 130.

Anodic polarizing circuit 50 (FIG. 4) contains a start relay comprising relay coil 510 and contactors 596 through 599. In the normally closed state contactor 599 connects line 111 to line 112 through lines 116 and 117 thereby bringing reference electrode 12 and test electrode 14 into a momentarily shorted condition. Similarly, contactor 598 connects lines 552 and 590 thereby bringing test electrode 14 and auxiliary electrode 16 into a momentarily shorted condition. One terminal of relay coil 510 is connected to a 24 v power supply through line 503, transistor 508, and lines 506 and 908 (FIG. 3A). The other terminal of coil 510 is connected to the anode of thyristor 504. Thyristor 504 is turned on by a signal received at its gate from contractor 1418 of cathodic timing circuit 140 through line 502.

In operation, a positive signal is passed through line 502 by cathodic timing circuit 140 after 120 seconds of its operation. Accordingly, relay coil 510 becomes energized and contactors 596–599 are moved to their normally open positions. Thyristor 504 may be reset by interruption of power on line 503 caused either by depression of reset button 162 (FIG. 7), by operation of comparator circuit 80 to be discussed infra, or by nonconduction of transistor 508.

Transistor 508 is a PNP type and is maintained in a conductive state by application of a negative current to the base thereof. This negative current is developed by NPN transistor 514. Transistor 514 is maintained in a conductive state by a positive current to its base. This positive current is derived from line 506 and passes through LED 516, diodes 517 and voltage divider 515. The current passing through LED 516 causes illumination thereof if thyristor 520 is conducting. LED 516 serves as an indication that the corrosion rate is less than 1 MPY. The base of transistor 514 may be grounded thus rendering transistor 508 nonconductive by switching thyristor 520 on at the end of the operation of circuit 50, as will be discussed.

Anodic polarization circuit 50 contains a timing integrator 518 which controls the timing function thereof. Timing integrator 518 contains a timing capaciter 519 which is discharged through contactor 596 and resistor 578 when contactor 596 is in its normally closed state. Movement of contactor 596 to the normally open position causes integrator 518 to be connected to an input voltage source through line 522. The input voltage source comprises a 5 volt supply which is connected through potentiometer 530 to the input of a buffer amplifier 532. The positive output of amplifier 532 is made available through line 534 to the normally open terminal of relay contactor 542. The output of amplifier 532 is also inverted in amplifier 540 thus making a negative voltage available to the normally closed terminal of relay contactor 542. The wiper of contactor 542 is connected through the normally closed terminal of a relay contactor 595 to relay contactor 596. Initially, the negative potential from the normally closed terminal of contactor 542 is presented to integrator 518 resulting in a linearly increasing command signal on line 543. This command signal is passed through buffer amplifier 544 to the non-inverting input of operational amplifier 546. The inverting input of amplifier 546 receives a current signal through line 590 from auxiliary electrode 16. The output of amplifier 546 drives transistor 550 thereby impressing a current on test electrode 14 through line 552 to anodically polarize that electrode. The rate of anodic polarization is set by potentiometer 530. This rate is preferably set at 2 ma per minute but can range from 0.5 ma to 10 ma per minute.

The output of integrator 518 is also delivered to operational amplifiers 566 and 573. Amplifier 566 receives this signal at its non-inverting input and compares it to a positive reference voltage derived from a 15 v source and a voltage divider comprising resistors 560, 562, and potentiometer 564. When the output of integrator 518 exceeds the voltage set at potentiometer 564, an output signal is passed from amplifier 566 through diode 594 and voltage divider 593 to the gate of thyristor 568. Thyristor 568 is connected to one terminal of relay coil 570. The other terminal of relay coil 570 is connected through contactor 597 to line 506. Accordingly, the output of amplifier 566 turns thyristor 568 on and thereby causes energization of relay coil 570. Coil 570 causes contactors 536 and 542 to assume their normally open positions. Consequently the positive voltage on line 534 is passed through contactor 542 to integrator 518 thereby causing the command signal output of integrator 518 and the current passed to test electrode 14 to decrease at the same rate as it increased, thus producing the reverse anodic current scan. The point of reversal is set by potentiometer 564 to be 50 ma but can range from a value of 0.5 ma to 500 ma.

Movement of contactor 536 to the normally open position causes a signal to be transmitted from anodic cell voltage measuring circuit 110 through line 592 to comparator circuit 60 as will be discussed in detail hereinafter.

Operational amplifier 573 receives the output of integrator 518 on line 574 and compares this output with a reference voltage derived from a −15 v supply and voltage divider 592. This reference voltage is set at a slightly negative value. Accordingly, if cathodic polarization circuit 50 is not reset by comparator 60, amplifier 573 produces an output signal on line 590 when the decreasing command signal on line 574 becomes slightly negative. The output signal on line 590 is passed through diode 589 and voltage divider 588 to the gate of thyristor 520. Operation of thyristor 520, as explained above, causes thyristor 504 to be reset.

It should be noted that the output of integrator 518 can be held constant by interruption of the input signal thereto. The input signal can be interrupted by energization of relay coil 580 which moves contactor 595 to its normally open position. Coil 580 may be energized by a signal produced by comparator 60.

Figure 5:
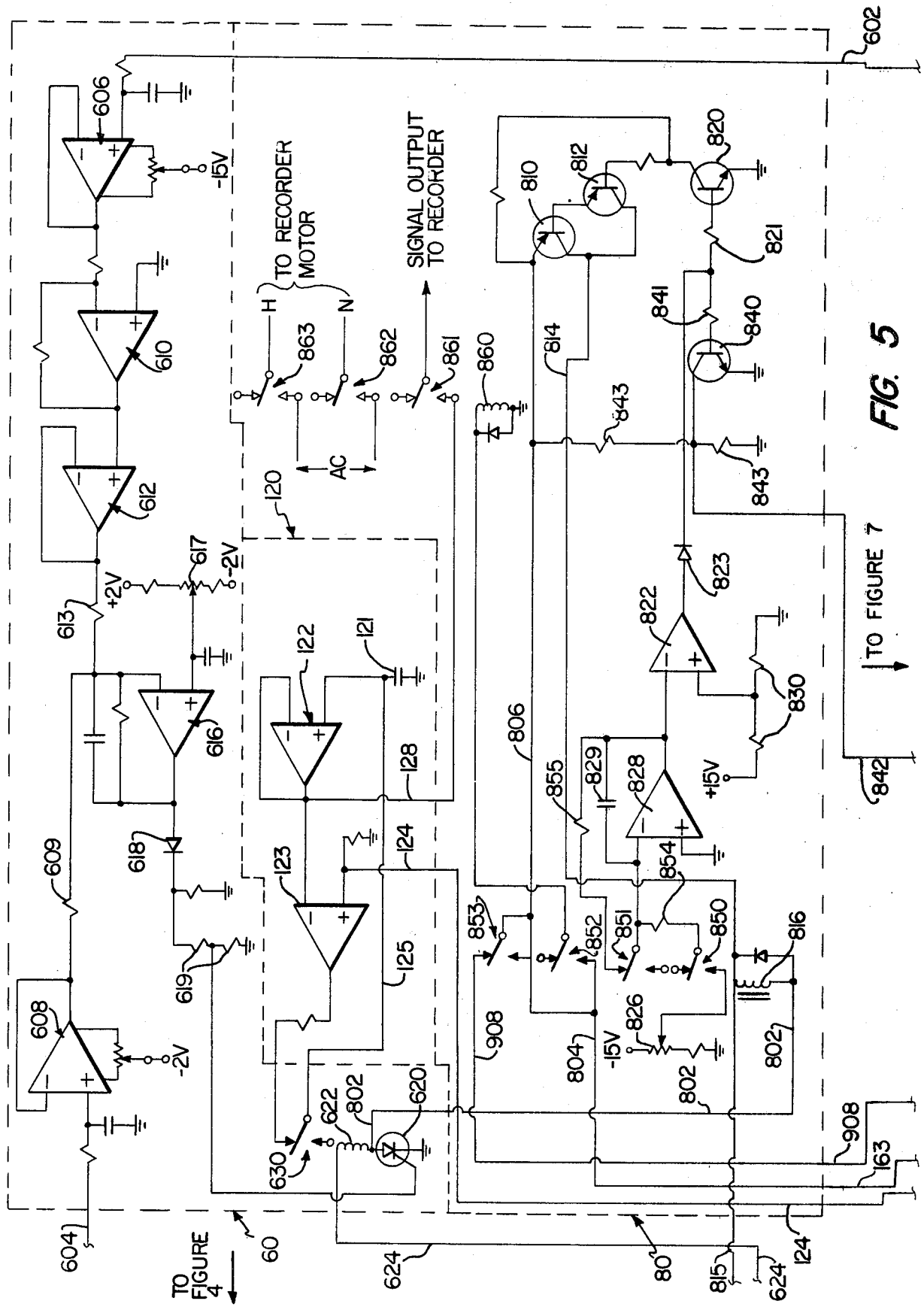
FIG. 5 is a detailed schematic diagram of the comparator circuit, anodic memory circuit, the recorder timing circuit of the present invention.

Anodic cell voltage measuring circuit 110 comprises buffer amplifiers 113 and 114 which receive signals on lines 111 and 112 respectively which signals are indicative of the voltage of reference electrode 12 and test electrode 14, respectively, during anodic polarization. The outputs of amplifiers 113 and 114 are tied to the non-inverting and inverting inputs, respectively, of differential amplifier 115. Accordingly, it can be seen that the output of amplifier 115 is indicative of the voltage of test electrode 14 with respect to reference electrode 12. During the reverse anodic scan of cathodic polarization circuit 50, this output signal is passed through contactor 536 and line 592 to comparator circuit 60 (FIG. 5).

A second input to comparator circuit 60 is produced by computer circuit 70 (FIG. 7). Computer circuit 70 receives the maximum log I signal on line 433, as discussed above. Computer circuit 70 also receives a signal on line 71 indicative of the current passing through auxiliary electrode 16 during the anodic polarization phase. This signal is referred to as log $I_A$. The log $I_A$ signal is generated by log amp 130 (FIGS. 3A and 3B), which receives a signal indicative of the current passing through auxiliary electrode 16 ($I_A$) on line 172 from the normally open terminal of contactor 109. Log amp 130 produces an output on line 1302 which is the logarithm of the signal received on line 172. This output signal (log $I_A$) is passed through contactor 108 to line 71.

Computer circuit 70 (FIG. 7) comprises an integrated circuit multiplier such as type AD534 sold by Analog Devices, Inc. Circuit 70 generates an output voltage on line 602 in accordance with the mathematical formula:

$$E_{out} = -0.280 [\log (I_A) - \max \log I] - 0.100 \text{ volts}$$

where:

$E_{out}$ = output voltage on line 602
log ($I_A$) = log of current during anodic polarization
max log (I) = log of maximum current during cathodic polarization The slope value, −0.280 per decade of current, is empirically based, and other values may be employed, as described below.

Comparator circuit 60 (FIG. 5) comprises input buffer amplifiers 606 and 608 which filter and buffer signals received on lines 602 and 604, respectively. The output of amplifier 606 is amplified and inverted in amplifier 610. The output of amplifier 610 is buffered in buffer amplifier 612 and passed through resistor 613 to the inverting input of amplifier 616. The inverting input of amplifier 616 also receives the output of amplifier 608 through resistor 609. The non-inverting input of amplifier 616 receives a reference voltage signal derived from a +2 v source and a −2 v source connected to opposite terminals of potentiometer 617. Amplifier 616 produces a positive output when the signal received at its inverting input is slightly less than the reference voltage signal from potentiometer 617. The reference voltage is approximately 0 volts, but can be slightly greater.

In operation, computer circuit 70 produces a cathodic curve extrapolation (FIG. 8) through the point (−0.100 v, maximum log I) at a slope of 0.280 volts per decade. This extrapolation is received on line 602 and subtracted from the reverse anodic current curve generated by anodic cell voltage measuring 110 and received on line 604. The difference signal is applied to the inverting input of amplifier 616. When the difference signal becomes less than the reference signal applied to the non-inverting input of amplifier 616, that amplifier produces an output signal which indicates the intersection of the cathodic curve extrapolation and the reverse anodic current curve.

The output of amplifier 616 is passed through diode 618 and voltage divider 619 to the gate of thyristor 620. The cathode of thyristor 620 is connected to gound. The anode of thyristor 620 is connected to one terminal of relay coil 622 and to line 802. The opposite terminal of relay 622 is connected to line 624. Line 624 is connected to relay coil 580 (FIG. 4). Accordingly, when thyristor 620 is turned on, relay coils 580 and 622 are energized. Relay coil 580 causes the current in test electrode 14 to remain constant, as discussed above. Relay coil 622 operates relay contactor 630. Contactor 630 is connected to anodic memory circuit 120.

Anodic memory circuit 120 comprises a memory capacitor 121 connected to the non-inverting input of buffer amplifier 122. The output of amplifier 122 is connected to the inverting input of operational amplifier 123. The non-inverting input of amplifier 123 is connected through line 124 to line 71 from which it receives the log $I_A$ signal. The output of amplifier 123 is passed through the normally closed terminal of contactor 630 and line 125 to capacitor 121.

In operation, operational amplifier 123 compares the charge on capacitor 121, received from amplifier 122, to log $I_A$, received on line 124, and charges or discharges capacitor 121 through line 125 to make the capacitor charge equal to log $I_A$. When contactor 630 moves to the normally open position, the charge on capacitor 121 remains constant and is equal to the value of log $I_A$ at the moment of intersection of the cathodic curve extrapolation and the reverse anodic curve. This value is the pitting current and is passed through line 128 to recorder timing circuit 80.

Recorder timing circuit 80 contains a timing integrator consisting of operational amplifier 828 and capacitor 829. The output of amplifier 828 is delivered to operational amplifier 822 where it is compared to a reference voltage derived from a +15 v supply and voltage divider 830. A positive output from amplifier 822 is passed through diode 823 to the bases of transistors 820 and 840 through resistors 821 and 841, respectively. A positive output from amplifier 822 causes transistors 820 and 840 to conduct. Conduction of transistor 840 shorts out resistor 843 and produces a low voltage output to be delivered through line 842 to repeat/delay circuit 40.

Conduction of transistor 820 causes transistors 810 and 812 to conduct also. The emitter of transistor 810 is connected to line 806 which is connected through line 804 and reset switch 162 to a +24 v supply. The collector of transistor 810 is connected to line 814. Accordingly, conduction of transistor 810 causes positive supply voltage to be available on line 814.

Line 842 is also connected to the positive supply on line 806 through resistor 843. Consequently, when transistor 840 is nonconductive, a positive output voltage is delivered through line 842.

The supply voltage on line 814 is delivered to one terminal of relay coil 816 and is also used to energize relay coils 580 and 622 through lines 815 and 624. The energization of relay coils 580 and 622 is discussed above. The opposite terminal of relay coil 816 is connected through line 802 to the anode of thyristor 620. Relay coil 816 operates relay contactors 850 to 853. Contactor 850 is operative in its normally open position to connect a voltage source comprising a −15 v supply and potentiometer 826 to the inverting input of amplifier 828 through resistor 854. Contactor 851 is operative in its normally closed position to connect resistor 855 in parallel circuit with capacitor 829 thus discharging that capacitor. Contactor 852 is operative in its normally open position to pass supply voltage from line 804 to relay coil 860 to energize that relay coil. Contactor 853 is operative in its normally closed position to pass supply voltage from line 804 to line 908.

Relay coil 860 operates contactors 861, 862 and 863. Contactors 862 and 863 pass AC supply voltage to a recorder (not shown). Contactor 861 is operative in the normally open position to pass the log $I_A$ signal on line 128 to the recorder. This signal is indicative of pitting current.

In operation, when relay coil 816 is energized, the timing integrator comprising capacitor 829 and amplifier 828 is connected to potentiometer 826. The output of the timing integrator begins to rise in accordance with the setting of potentiometer 826. When the output of amplifier 828 reaches the level set by voltage divider 830, the output of amplifier 822 becomes negative. Transistors 820 and 840 become nonconductive. The output on line 842 becomes positive and the voltage supply on line 814 is removed, thus resetting the circuits connected thereto.

Also, when coil 816 is energized, relay 860 becomes energized causing the pitting current signal on line 128 to be recorded. Finally, the supply voltage on line 908 is interrupted causing all circuits connected thereto to be reset.

Repeat/delay circuit 30 (FIG. 7) comprises a delay section which produces a time delay signal derived from an AC source 602. The signal from source 602 is filtered in filter section 604 and amplified by amplifier 606. The amplified signal is half wave rectified by diode 608 and fed through transistor 610 to a wave shaping circuit comprising NAND gates 612, 614 and 616. NAND gates 612, 614 and 616 transform the output from transistor 610 into square pulses which are fed to counter 618. Counter 618 contains four 74LS90N integrated circuits and three 74LS92N integrated circuits wired in series to produce a total divide by $2.16 \times 10^6$. The output of counter 618 is delivered to counter 619 which provides BCD coded output to decoder 620, which provides appropriately divided outputs to switch 621. Accordingly, it can be seen that an operator may select any desired time delay by adjusting switch 621. The output of switch 621 is inverted in NAND gate 650.

Counters 618 and 619 may be reset by receipt of a reset signal from lines 622 and 623, respectively. The reset signal is delivered from a +5 v source through resistor 624. In order for the counters to operate, transistor 625 must be conductive. Transistor 625 can be made conductive by receipt of a signal through line 626 and filter network 627.

Repeat/delay circuit 30 also includes a repeat relay coil 680, one terminal of which is connected to thyristor 681. The gate of thyristor 681 is connected to a switch 682 which can be moved between an off terminal position 683 and a repeat terminal position 684. The opposite terminal of coil 680 is connected through line 686, contactor 903 (FIG. 3A), line 685 and reset switch 162 to a +24 v supply.

Relay coil 680 operates contactors 678 and 679. Contactor 678 connects line 626 to ground when in the normally closed position. When in the normally open position contactor 678 connects a +5 v source to line 626. In its normally open position, contactor 679 connects the output of NAND gate 650 through resistor 690 to the base of transistor 691. The collector of transistor 691 is connected to the base of transistor 692. The emitter and collector of transistor 692 are connected to opposite terminals of start switch 161. Conduction of transistor 692 causes a positive voltage to be applied to line 909 to repeat the meter sequence.

In operation, if switch 682 is in the off position 683 when a signal is received on line 842, no additional action of the meter occurs.

If switch 682 is in the restart position 684, a signal on line 842 turns thyristor 681 on. Coil 680 is energized and contactors 678 and 679 move to their normally open positions. Consequently, transistor 625 is made conductive and counter 618 starts counting pulses received from NAND gate 616. After the appropriate delay period set by switch 621, a voltage is passed through NAND gate 650 and causes transistor 692 to conduct. Accordingly, the operation of the meter is restarted and the sequence of operations described above repeats.

ALTERNATE EMBODIMENTS

Instead of using the empirically based value of 0.280 volt per decade of current for the slope of the cathodic curve extrapolation, information as to the slope may be obtained by locating a second point on the extrapolation. In one embodiment of such procedure, test electrode 14 was polarized to −0.010 volts from its rest potential (employing reference electrode 12 as a reference for the polarization) and held there for five minutes by means of a circuit like cathodic polarization circuit 20. At the end of that time, the current being passed between auxiliary electrode 16 and test electrode 14 was noted and stored by a circuit like circuit 40. This value is related to Point B in FIG. 8. (Due to curvature through zero net current at the open circuit (corrosion) potential, the 0.010 v cathodic polarization point is not on the straight line portion of the cathodic curve or its extrapolation and the current at that polarization must be multiplied by a value averaging 4.0 to arrive on the straight line.) Electrode 14 was then further cathodically polarized by means of a circuit like circuit 20 at a 4 volts per hour rate to −0.100 volt. Again, after five minutes, the corresponding current between auxiliary electrode 16 and test electrode 14 was noted and stored by a circuit like circuit 40. This value corresponds to Point A in FIG. 2. Points A and B were used to generate the slope and intercept of the cathodic curve extrapolation, a circuit like circuit 60 being employed for this purpose.

Comparisons between typical data obtained from the pitting rate meter ("pit meter") method of this invention with the non-linear polarization method are shown in the following Table, the "pit meter" data in this case being obtained using the alternate two point method described above for determining the slope of the cathodic curve extrapolation:

| Comparison of Pit Meter Pitting Data Against That Obtained Using Non-Linear Polarization | | |
|---|---|---|
| Pitting Rate (Mils penetration per year) | | Percent |
| Polarization | Pit Meter | Difference |
| 840 | 900 | 6.7 |
| 950 | 970 | 2.1 |
| 880 | 880 | 0 |
| 180 | 170 | 5.6 |
| 107 | 106 | 0.1 |
| 11 | 12 | 8.3 |
| 47 | 47 | 0 |
| +1100 | 1100 | 0 |
| +1100 | 1100 | 0 |
| +1100 | 1150 | 4.6 |
| 620 | 660 | 6.1 |
| 580 | 500 | 13.8 |
| +480 | 520 | 7.7 |
| +480 | 540 | 11.1 |
| 410 | 450 | 8.9 |
| 1400 | 1480 | 5.4 |
| 110 | 140 | 21 |
| 170 | 140 | 17.7 |
| ++75 | 79 | 5.1 |
| ++15 | 17 | 11.8 |
| ++15 | 12 | 20.0 |

+Repetitive Tests
++Data obtained from field tests

As can be seen from the Table, the two methods yield substantially identical pitting rate data. The pit meter method has the advantage of being automatic and not requiring corrosion expertise for its utilization.

As indicated above, the anodic polarization may be carried out by varying (first increasing and then decreasing) either the current or the potential between the test and auxiliary electrodes. In general, polarization, anodic or cathodic, can be done in two different ways; one is potential control, called potentiostatic or potentiodynamic control, depending on whether the potential is held or scanned; and the other is current control, called galvanostatic or galvanodynamic control for the same reasons. The meter can function using either current control or potential control. Only a change in the anodic polarization circuit 50 is involved.

The −0.100 volt point for cathodic polarization is not critical. A point anywhere between −0.010 and −0.500 volt may usefully be employed, for example, from −0.075 to −0.120 volt.

The use of a single test electrode wherein both cathodic and anodic polarizations are done on the same test electrode is preferred, with the cathodic polarization kept to voltages not substantially exceeding 100 mv. Such voltages do not irreversibly alter the film character of the electrode as would greater polarization, e.g., using 300 mv as in prior art procedures. Thus, the meter starts the anodic polarization step on an electrode that is still essentially in equilibrium with the corrodant.

Where voltages substantially exceeding 100 mv are employed for cathodic polarization, accuracy may be insured if separate anodic and cathodic test electrodes are employed.

Although the slope of the cathodic curve extrapolation is optimally assumed to be 0.280 per decade of current in the preferred procedure of this invention, the slope could vary from 0.06 v to 10 v, for example from 0.120 v to 2 v, but ordinarily from 0.200 to 0.400 volt per decade, depending on the properties of the electrode surface film and the corrosive fluid. The slope value used as optimum is an average of the slopes in systems where pitting is a consideration. Determination of the exact slope in each case involves a slow (e.g. 1 to 4 volts per hour) scan of cathodic potentials starting at the corrosion potential of the test electrode.

Similarly, the −0.010 volt point used in the alternate cathodic polarization procedure is also not critical. A point anywhere between −0.002 and −0.050 volt may be usefully employed, for example, from −0.005 to −0.025 volt, and preferably from −0.008 to −0.012 volt. When −0.010 volt is used, the current value is multiplied by 4 to determine the actual point on the cathodic extrapolation, as explained above.

The two minute holding time for the −0.100 volt cathodic polarization potential in the preferred procedure and the five minute holding time for both the 0.100 volt point and the 0.010 volt point in the alternate procedure are likewise not critical. A period varying from 0 to 1 hour may be utilized in each case, for example, from 10 seconds to 15 minutes, and preferably from 0.5 to 2.5 minutes.

The anodic polarization limit (anodic current at reversal) is not critical and may suitably vary from 0.05 to 50 milliamperes per square centimeter of test electrode surface area, for example, from 0.5 to 10 ma/cm$^2$, with 2.0 to 7.0 ma/cm$^2$ being preferred, about 5.0 ma/cm$^2$, which amounts to 50 milliamperes for a standard size electrode, is optimum, as indicated above. The rate of current increase can be from 0.1 to 50 milliamperes per minute, suitably 0.5 to 20 milliamperes per minute and preferably 1 to 5 milliamperes per minute, with 2 milliamperes per minute being optimum. The reverse scan rate does not have to be identical with that of the forward scan but making it identical gives better accuracy and allows for simplification of circuitry.

The recording and display time for the pitting rate may suitably be for a period up to 60 minutes and more suitably not more than 30 minutes. One minute is ordinarily sufficient.

Instead of increasing the current to the desired value in the anodic polarization, the electrode potential may, alternatively, be raised until the desired current is attained. The range of voltage rate increase and/or decrease may be as high as 50 volts per hour, more suitably not more than 10 volts per hour, and preferably 1 to 5 volts per hour.

The position of the intersection Point D or E in FIG. 8 depends on the shape and position of the reverse anodic curve. In some corrosion systems, the reverse anodic curve will approach zero current at a potential positive to the starting open circuit (i.e., rest) potential; then the intersection would be at a Point such as E. In other systems, the reverse anodic curve will be negative to the starting potential; the intersection then would be at a Point such as D. It is also possible that the anodic curve could approach zero current at nearly the starting circuit potential. The fundamental reason for these variations is that removing spots of the surface film on the anodic scan (which gives the positive hysteresis in the first place) also has an effect on cathodic activity. If removing spots of film gives more increase in cathodic activity than in anodic activity, then the return potential will be more positive than the starting (completely filmed) potential. If, on the other hand, the creation of relatively bare spots increases anodic more than cathodic activity, the return potential will be negative to the starting potential. In the event that anodic and cathodic activities are equally increased, the two potentials will be the same. The pitting rate determination is equally valid under any of the three conditions.

It will be evident that the foregoing description is illustrative of, rather than limitative upon, the invention as defined by the appended claims and that various changes and modifications can be made in the apparatus, circuits and methods exemplified without departing from the spirit of the invention.

We claim:

1. A pitting corrosion meter comprising:
   test electrode means for immersion in a corrodant fluid;
   reference electrode means for immersion in said corrodant fluid;
   auxiliary electrode means for immersion in said corrodant fluid;
   cathodic circuit means for cathodically polarizing said test electrode means with respect to said reference electrode means thereby causing current flow in said auxiliary electrode means;
   first monitoring means for monitoring said current flow and storing a peak value of said current flows;
   computer circuit means for producing a cathodic polarization curve and its extrapolation containing said peak value;
   anodic circuit means for increasingly anodically polarizing said test electrode means with respect to said reference electrode means to a first predetermined value, and thereafter decreasingly anodically polarizing said test electrode means with respect to said reference electrode means;
   second monitoring means for monitoring the anodic current and corresponding potentials of said test electrode means with respect to said reference electrode means during said decreasing anodic polarization of said test electrode means, thereby generating a reverse anodic polarization curve; and
   comparator means for determining the point of intersection between said reverse anodic curve and said cathodic curve or its extrapolation.

2. The meter defined in claim 1 and further including display means for displaying a value indicative of said point of intersection.

3. The meter defined in claim 2 wherein said display means includes a recorder means for recording said value indicative of said point of intersection.

4. The meter defined in claim 2 and further including repeat/delay circuit means responsive to said display means for selectively stopping meter operation or repeating meter operation after a time delay.

5. The meter defined in claim 4 wherein said time delay is produced by delay circuit means including pulse producing means for producing pulses at a predetermined frequency and counter means for receiving said pulses.

6. The meter defined in claim 5 and further including switch means connected to said delay circuit means for selecting a delay interval.

7. The meter defined in claim 6 wherein said pulse producing means includes a voltage source for supplying a 60 hz input signal.

8. The meter defined in claim 1 wherein said anodic circuit means for anodically polarizing the test electrode with respect to the reference electrode consists of circuit means for varying the current between the test and auxiliary electrodes at a fixed rate.

9. The meter defined in claim 1 wherein said anodic circuit means for anodically polarizing the test electrode with respect to the reference electrode consists of circuit means for varying the potential of the test electrode with respect to the auxiliary electrode at a fixed rate.

10. The meter defined in claim 1 wherein said test electrode means comprises a single test electrode.

11. The meter defined in claim 1 wherein two test electrodes are employed, one for the cathodic polarization and one for the anodic polarization.

12. The meter defined in claim 1 wherein said cathodic circuit means comprises first operational amplifier means connected to said test electrode means and said reference electrode means for producing an output indicative of the potential difference between said test electrode means and said reference electrode means.

13. The meter defined in claim 12 wherein said cathodic circuit means further includes second operational amplifier means for comparing the output of said first operational amplifier means to a reference voltage source, said second operational amplifier means having an output connected to said test electrode means for impressing a negative voltage thereon.

14. The meter defined in claim 1 wherein said first monitoring means includes a peak detector circuit means for determining said peak current.

15. The meter defined in claim 14 wherein said first monitoring means further includes storage circuit means including a storage capacitor for connection to said peak detector circuit means for storing a signal indicative of said peak current.

16. The meter defined in claim 15 wherein said storage circuit means further includes compensation means for producing a positive feedback signal to compensate for leakage current in said storage capacitor.

17. The invention defined in claim 16 wherein said peak detector circuit means includes a peak detector storage capacitor; means for comparing a charge on said peak detector storage capacitor to said current flow in said auxiliary electrode; circuit means responsive to said comparing means for charging said storage capacitor if said charge is below the level of said current flow; and circuit means responsive to said means for comparing for maintaining said charge constant if said charge is greater than the level of said current flow.

18. The invention as defined in claim 1 wherein said cathodic circuit means further includes timing means for activating said first monitoring means.

19. The invention as defined in claim 18 wherein said timing means includes timing integrator means for producing an output signal having a predetermined slope.

20. The invention as defined in claim 19 and further wherein said timing means includes first timing comparator means for comparing said timing integrator output signal to a first reference value and producing a first timing output dependent upon the relationship of said timing integrator output signal and said first reference value.

21. The invention as defined in claim 20 and further wherein said timing means includes second timing comparator means for comparing said timing integrator output signal to a second reference value and producing a second timing output dependent upon the relationship of said timing integrator output signal and said second reference value.

22. The invention defined in claim 1 wherein said anodic circuit means includes timing integrator means for producing an anodic polarization command signal having a predetermined slope in response to an input signal of a predetermined polarity.

23. The invention as defined in claim 22 wherein said anodic circuit means further includes comparator means for sensing said command signal and producing a reversing signal when said command signal reaches a predetermined value; and circuit means for reversing the polarity of said input signal in response to said reversing signal.

24. The invention as defined in claim 23 and further including current control circuit means responsive to said command signal for impressing a positive current on said test electrode means.

25. The invention as defined in claim 1 and further including mode select circuit means for selectively connecting said cathodic circuit means and said anodic circuit means to said test electrode means.

26. The invention as defined in claim 25 wherein said mode select circuit means includes a relay.

27. The invention as defined in claim 25 and further including timing circuit means connected to said mode select circuit means for changing said mode select circuit means between a first operative state wherein said cathodic circuit means is connected to said test electrode means, and a second operative state wherein said anodic circuit means is connected to said test electrode means.

28. The invention as defined in claim 27 and further including log amplifier means for logarithmically converting an input signal, said mode select circuit means being operative in one state to connect said log amplifier means to said first monitoring circuit and being operative in the other state for connecting said log amp means to said computer circuit means.

29. A pitting corrosion meter comprising:
one or two test electrodes, a reference electrode and an auxiliary electrode, said electrodes being adapted for immersion in a corrodant fluid;
circuit means for cathodically polarizing a said test electrode away from its rest potential to a predetermined negative potential with respect to said reference electrode and holding said test electrode at said predetermined potential for a predetermined period of time;
circuit means for reading and storing the value of the resulting current between said test and auxiliary electrodes, said value corresponding to a point on a semilogarithmic cathodic polarization curve
circuit means for generating said cathodic polarization curve and its extrapolation from one said reading and from stored information as to the slope of said curve or from two said readings at different predetermined negative potentials or from potentiodynamic cathodic polarization;
circuit means for increasing the current or potential between a said test and auxiliary electrode at a fixed rate to a predetermined value in order to anodically polarize said test electrode with respect to said reference electrode, then decreasing the current or potential at a fixed rate; the values of the anodic current at their respective potentials corresponding to a forward anodic polarization curve and a reverse anodic polarization curve;
circuit means for determining the intersection of said reverse anodic polarization curve with said cathodic polarization curve or its extrapolation by monitoring the individual values of the decreasing anodic current and their respective potentials, the value of the current at said intersection being that of the pitting current; and
means for displaying and/or recording said pitting current, said pitting current being proportional to the pitting rate.

* * * * *